United States Patent [19]
Sorgente et al.

[11] Patent Number: 6,162,787
[45] Date of Patent: Dec. 19, 2000

[54] METHODS FOR TREATING ARTHRITIS USING COLLAGEN TYPE II, GLUCOSAMINE CHONDROITIN SULFATE, AND COMPOSITIONS

[75] Inventors: Nino Sorgente, San Clemente; Robert M. Nakamura, La Jolla, both of Calif.

[73] Assignee: Immudyne, Inc., Houston, Tex.

[21] Appl. No.: 09/285,538

[22] Filed: Apr. 2, 1999

[51] Int. Cl.$^7$ .................................................. A61K 38/00
[52] U.S. Cl. .................................. 514/2; 514/8; 514/825; 514/54; 514/62; 424/184.1
[58] Field of Search ..................... 514/54, 62, 2, 514/8, 825; 424/184.1

[56] References Cited

U.S. PATENT DOCUMENTS

| | | | |
|---|---|---|---|
| 4,804,745 | 2/1989 | Koepff et al. | 530/356 |
| 5,364,845 | 11/1994 | Henderson | 514/54 |
| 5,399,347 | 3/1995 | Trentham et al. | 424/184.1 |
| 5,645,851 | 7/1997 | Moore | 424/439 |
| 5,843,445 | 12/1998 | Weiner et al. | 424/184.1 |
| 5,925,736 | 7/1999 | Neff et al. | 530/356 |

*Primary Examiner*—James H. Reamer
*Attorney, Agent, or Firm*—Thomas Fitting

[57] ABSTRACT

The invention describes compositions and methods for treatment of rheumatoid arthritis and osteoarthritis. The compositions comprise insoluble, native collagen Type II in a particular form in combinations with other active agents, including glucosamine, chondroitin, ascorbate, boron and magnesium. Also described are methods for producing particulated insoluble native collagen Type II.

29 Claims, No Drawings ly decomposed in a formulation for oral consumption to treat arthritis.

METHODS FOR TREATING ARTHRITIS USING COLLAGEN TYPE II, GLUCOSAMINE CHONDROITIN SULFATE, AND COMPOSITIONS

TECHNICAL FIELD

The present invention provides a method for the isolation and purification of insoluble, native collagen and chondroitin sulfate from cartilages, a therapeutic method and nutriceutical formulation containing therapeutic amounts of collagen Type II, glucosamine and/or chondroitin sulfate and/or magnesium ascorbic phosphate, and/or boron for the treatment of rheumatoid arthritis and osteoarthritis in humans and animals.

BACKGROUND OF THE INVENTION

The cartilage of the joints is called hyaline cartilage (from the Greek "hyalos" which means glass); hyaline cartilage is found not only on all surface of bones that move (articular cartilage) but also in the nose, larynx, ribs and trachea. This cartilage consists of 70% water, about 10% collagen Type II, and the rest is various protein and specialized complex sugars, called proteoglycans. The collagen and the proteoglycans form a meshwork that confers upon this cartilage stiffness, viscoelasticity, and durability. The articular cartilage provides load bearing, resilience, a low friction surface and distributes the load over the entire synovial joint. Even though the articular cartilage is very thin (about one eighth of an inch thick) it performs its function for the life of the individual (80–90 years or more) without any significant deterioration, unless it becomes injured or diseased.

There are two major diseases that affect cartilage, namely osteoarthritis and rheumatoid arthritis; both osteoarthritis and rheumatoid arthritis result in degradation and degeneration of the articular cartilage. Osteoarthritis is a disease of cartilage only and does not have an immunological component. The major symptoms of osteoarthritis are pain, stiffness, crackling, and enlargement and deformities of the affected joints; at the early stage of osteoarthritis there is little inflammation and swelling of the joints, however in advanced stages swelling and inflammation is usually present. Rheumatoid arthritis is an autoimmune systemic disease accompanied by severe inflammation of the joints. In most patients rheumatoid arthritis begins with a general feeling of malaise, fatigue, often accompanied by diffuse musculoskeletal pain. Eventually the disease progresses resulting in pain on motion, tenderness, swelling and deformation of multiple joints; because rheumatoid arthritis is a systemic disease, it may be accompanied by extra-articular complications, such as anemia, vasculitis, scleritis, pleurisy, pericarditis, and peripheral neuritis.

The accepted modality of treatment is a regimen of nonsteroidal anti-inflammatory drugs, particularly of the aspirin type, aimed primarily to reduce pain and inflammation, maintain joint mobility, and prevent deformity. In severe cases of rheumatoid arthritis gold compounds and certain cytotoxic drugs are often used. Even though these drugs may resolve symptoms, they do not alter the course of the disease. To arrest the course of the disease, it is necessary to eliminate the cause of the disease and to rebuilt the degraded cartilage. In rheumatoid arthritis terminating the immune reaction should arrest the course of the disease; in osteoarthritis, inhibition of the enzymes that degrade the extracellular matrix, i.e., collagenase and chondroitinases, should arrest the progression of the disease. Administration of glucosamine should facilitate rebuilding the degraded cartilage.

In the last few years novel approaches to the treatment of osteoarthritis and rheumatoid arthritis have emerged. Drovanti et al, *Clinical Therapeutics*, 3:260–272 (1980), reported that oral glucosamine sulphate is effective in the treatment of osteoarthritis. Fassbender et al, *Ostheoarthritis and Cartilage*, 2:61–69 (1994), have reported that glucosamine is more effective in the treatment of osteoarthritis than ibuprofen. Pipitone, *Drugs Exper. Clin. Res.*, 17:3–7 (1991), has reported that chondroitin sulfate protects cartilage from degradation. Trentham et al, *Science*, 261:1727–1730 (1993), reported that oral administration of a soluble form of collagen Type II resulted in significant improvement of rheumatoid arthritis symptoms. Barnett et al, *Arthritis and Rheumatism*, 39:623–628 (1996), also reported that administration of collagen Type II resulted in beneficial effects in patients suffering from Juvenile rheumatoid arthritis.

Boron appears to have some beneficial effects on some form of arthritis (Nwenham, *Environ Health Perspect*, 102:Suppl 7:83–85, 1994) however, its precise mechanism is not known. It is possible that boron acts by inhibiting the activated kallikrein-kinin system which appears to be operative in chronic inflammatory arthritis (Colman et al, *Proc Assoc Am Physicians*, 109:10–22, 1997).

Two nutritional supplements, namely chondroitin sulfate and glucosamine, have been used extensively in animals and man and have been shown to be effective in alleviating osteoarthritis (Theodosakis et al, in "The Arthritis Cure" St. Martin Press, New York, 1997). Vitamin C has been shown to be a critical agent for the normal synthesis and assembly of newly synthesized collagen. Collagen Type II has been used to treat rheumatoid arthritis in humans with some success, Barnett et al, "Treatment of Rheumatoid arthritis with oral Type II collagen", in *Arthritis and Rheumatism*, 41:290–297 (1998). In addition boron has been shown to be beneficial to patients suffering with osteoarthritis and to be beneficial for normal health of bone and joints (Nwenham, *Environ Health Perspect.*, 102:Suppl 7:83–85, 1994).

U.S. Pat. No. 5,399,347 describes the use of collagen Type II or biologically active collagen peptides for the treatment of rheumatoid arthritis. U.S. Pat. No. 5,529,786 describes the use of animal tissue containing Collagen Type II for the treatment of rheumatoid arthritis. U.S. Pat. No. 5,364,845 describes the use of combined glucosamine, chondroitin sulfate and manganese for the treatment of osteoarthritis.

U.S. Pat. No. 5,529,786 has described the preparation of Type II collagen for use in treating rheumatoid arthritis, although the collagen is crudely prepared in various forms such as "diced cartilage", liquid nitrogen cartilage powder and acetic acid soluble collagen.

BRIEF SUMMARY OF THE INVENTION

It has now been discovered that collagen Type II in an insoluble native form is particularly useful for oral administration to treat arthritis. Thus, the invention describes a procedure to purify large quantities of insoluble, native collagen Type II from cartilage, and at the same time purify chondroitin sulfate from the same cartilage. The invention also describes a formulation for use in a composition for treating rheumatoid arthritis and osteoarthritis that comprises native insoluble collagen Type II according to the present invention in combination with glucosamine, chondroitin sulfate and/or other medicaments.

The collagen alleviates the inflammation due to an autoimmune reaction that is prevalent in rheumatoid arthritis and which very likely is responsible for the inflammation that occurs in late osteoarthritis. The glucosamine and chondroitin sulfate facilitate the regeneration of cartilage by providing a substrate for the synthesis of cartilage polysaccharides and inhibiting the enzymes that degrade cartilage. The synergy from the combined therapeutic strategies provides increased healing and prevention of disease.

DETAILED DESCRIPTION OF THE INVENTION

The invention describes methods and compositions for the treatment of rheumatoid arthritis and osteoarthritis and other conditions that manifest cartilage degradation and inflammation particularly of the joints, but including other cartilages. Rheumatoid arthritis usually refers to an autoimmune systemic disorder that is accompanied by severe inflammation of the joints. Osteoarthritis is not an immunological disorder and is not a systemic disease, it affects only cartilage. However, the end result of both diseases on cartilage is the same, namely degradation and destruction of cartilage associated with pain, swelling, inflammation, joint enlargement and deformity.

In the intestine, the presentation of an antigen to the immune system is mediated by the cells of the Peyer's patch. Like all antigen presenting cells, Peyer's patch cells respond more easily to large, particulate antigens than to small soluble antigens. It is therefor preferred that the collagen Type II antigen used in the present case be in an insoluble particulate form to elicit a greater response.

A. Methods for Purification of Insoluble Native Collagen Type II

The present invention describes a process for the purification of an insoluble collagen Type II from cartilage in a form that is highly effective in eliciting immunological tolerance when administered as an oral composition. The invention also describes methods for the purification of chondroitin sulfate from the same cartilage processed by the present methods for isolating insoluble collagen.

To that end, cartilage is first collected by isolating sections of tissue containing cartilage, such as sternum, scapula, nasal septum, and the like tissues. Cartilage is then cleaned of all adhering soft tissues and of the perichondrium, diced into small pieces of about 0.2 to 5 cm$^2$, preferably about 0.5 to 2 cm$^2$, and extracted with 0.5 to 5.0 molar (M), preferably about 1.0 M, guanidinium hydrochloride; after 24–48 hours the remaining insoluble cartilage pieces (collagen) are separated from the liquid by filtration. The cartilage retained by the filter is comprised mostly of insoluble collagen, whereas the liquid filtrate contains chondroitin sulfate and other components which is collected and retained for later use in purifying chondroitin sulfate. The filter retentate material is harvested and designated insoluble native collagen Type II, unproteolyzed.

In one embodiment, the collagen in the insolubilized cartilage is further purified by enzymatic digestion (e.g., 0.2–1.0% protease, preferably 0.5% pepsin) in an acidic solution of about pH 1–4 in the presence of a high concentration of salt in the range of about 0.5 to 2 molar, where the digestion is carried out for a time period of about 24–72 hours. Any salt may be used at this step, although preferred salts include sodium chloride, potassium chloride, guanidinium chloride, and the like salts. The salt is then removed by successive washes in aqueous ethanol, preferably about 20% ethanol, on a filter to collect proteolyzed insoluble collagen Type II.

Amino acid analysis can be used to assess the purity of the collagen. The collagen is then milled using a centrifugal mill or other similar equipment, to a particle size from 1 to 100 microns (u), preferably about 10 to 75 u, more preferably about 25 to 40 u, and allowed to air dry at room temperature to form a collagen powder. The milling can be conducted by any of a variety of methods. The sizing of the particles can be carried out by use of mesh screens sized to isolate a particular size class of particles. Mesh screens are well known, and therefore the sizing method is not considered to be limiting.

The collagen in powdered form of 1 to 100 u sized particles is used to prepare compositions in the form of tablets, capsules and the like to treat man and other mammals who suffer with arthritis by oral administration of the composition.

Preferred methods for the preparation of insoluble collagen according to the present invention are described further in the Examples.

B. Methods for Purification of Chondroitin Sulfate

To purify chondroitin sulfate, the collected filtrate liquid described above is dialyzed against 0.1 M Na-acetate, pH 5.5, containing 5 mM cysteine and 5 mM EDTA. Papain (6 mg/ml) is added to dialyzate and incubated for 24 h at 65 C. The incubation is terminated by addition of trichloroacetic acid to a final concentration of 5% (w/v) and the resulting precipitate is removed by centrifugation, and the supernatant is dialyzed against de-ionized water. Chondroitin sulfate is precipitated by slowly adding 0.1% cetylpiridinium chloride to the dialysate. The resulting precipitate is then redissolved in 2 M NaCl, reprecipitated with 80% ethanol and finally redissolved in water to form purified chondroitin sulfate.

C. Methods For Treatment of Arthritis

The methods and composition of the present invention rely on the oral administration of a composition comprising collagen Type II in combination with glucosamine (and/or its salts) and/or chondroitin sulfate (and/or its salts). The composition may also comprise vitamin C, boron and any of a variety of nutritional supplements as is described further herein.

The administration of collagen Type II according to the present invention induces oral tolerance thus inhibiting the immune component of the disease, namely inflammation, swelling, and redness. Typical dosages in a composition of the invention are in the range of 1 microgram (ug) to 5 milligram (mg), preferably about 10–100 ug, and more preferably about 40 ug per 70 kg adult per day.

Glucosamine and chondroitin sulfate enhance the synthesis of cartilage polysaccharides and inhibit the enzymes that degrade cartilage macromolecules. Preferred methods and composition of the present invention rely on the combination of collagen Type II with one or both of glucosamine and chondroitin sulfate. Typical dosages of glucosamine in a composition of the invention are in the range of 50–1000 mg, preferably about 100–600 ug, and more preferably about 300 ug per 70 kg adult per day. Typical dosages of chondroitin sulfate in a composition of the invention are in the range of 50–1000 mg, preferably about 100–800 ug, and more preferably about 400 ug per 70 kg adult per day.

Vitamin C (ascorbate), a necessary cofactor for the synthesis of collagen, is also included in preferred embodiments. Typical dosages of ascorbate in a composition of the invention are in the range of 1–500 mg, preferably about 100 ug per 70 kg adult per day.

Boron, which prevents calcium and magnesium loss, is also included in the preferred embodiments. Typical dosages of boron in a composition of the invention are in the range of 0.5–20 mg, preferably about 6 mg per 70 kg adult per day.

Magnesium prevents calcium loss from bone, and thereby prevent weakening of the bone structures supporting cartilage. Magnesium also supports cartilage biosynthesis and thereby provides multiple benefits in composition of the invention. Magnesium is provided as elemental magnesium and can be formulated as any salt, preferably magnesium ascorbate. Typical dosages of magnesium in a composition of the invention are in the range of 0.1–10 mg, preferably about 5 mg per 70 kg adult per day.

The reagents for use in a composition of the present invention, such as glucosamine, chondroitin sulfate, ascorbate, boron, and magnesium in the various forms, can be obtained from a variety of sources, and therefore the invention is not to be construed as so limited.

Thus, the invention contemplates a method for treating rheumatoid arthritis or osteoarthritis in a patient comprising oral administration of an effective amount of a composition comprising collagen Type II and a compound selected from the group consisting of glucosamine salt and chondroitin salt. Typically the glucosamine salt is glucosamine sulfate and the chondroitin salt is chondroitin sulfate. The composition may optionally further comprise boron, ascorbic acid or magnesium salt in any of a variety of bioavailable forms and either alone or in combination.

In one embodiment, the composition comprises collagen Type II and glucosamine salt. In another embodiment, the composition comprises collagen Type II and chondroitin salt. More preferably, a composition comprises collagen Type II, glucosamine and chondroitin salt. Particularly preferred compositions are described in the formulations described herein below.

The collagen Type II used in a composition of this invention is an insoluble and native form of collagen as described herein, and is provided in the form of particles having a size of 1 to 100 microns. A preferred collagen Type II is prepared according to the methods described herein.

The composition of this invention can be administered orally following a schedule and at a concentration that is effective in alleviating the pain, swelling and inflammation associated with rheumatoid arthritis and osteoarthritis. The amount of ingredients depends on a number of factors such as the schedule of administration, the form of the supplements, and the like, with exemplary amounts typically being a combination of 20 micrograms of collagen Type II, 250 mg of glucosamine and 250 mg of chondroitin sulfate, and 100 mg of Vitamin C and 3 mg of boron administered in the form of a tablet or capsule once in the morning and once in the evening at least 30 minutes before meals.

It will also be possible to incorporate the supplements of the present invention into control-release formulations, where the total amounts of the supplements will be released over time. The formulations of the present invention may also contain auxiliary compounds, such as binders, vitamins, amino acids, fillers, gelatin, etc.

The composition of this invention can be administered multiple times a day, such as from 1 to 6 times daily although 1–2 daily dosages are preferred. Furthermore, the composition can be formulated into a variety of formats, for administration in unit dosages such as a tablet, capsule, powder, suspension and aerosol spray, and the like.

The following formulations for the treatment of rheumatoid arthritis and osteoarthritis is exemplary of a composition of this invention.

Formula 1

| Component | Amount |
| --- | --- |
| Insoluble Collagen Type II (1 to 100μ) | 5 μg to 1 mg |
| Glucosamine sulfate | 100 to 300 mg |
| Chondroitin sulfate | 100 to 300 mg |
| Magnesium ascorbic phosphate | 100 mg |
| Cellulose | 20 mg |
| Sucrose | 5 mg |

Formula 2

| Component | Amount |
| --- | --- |
| Insoluble Collagen Type II (25 to 40μ) | 5 μg to 1 mg |
| Chondroitin sulfate | 100 to 300 mg |
| Magnesium ascorbic phosphate | 100 mg |
| Cellulose | 20 mg |
| Sucrose | 5 mg |

Formula 3

| Component | Amount |
| --- | --- |
| Insoluble Collagen Type II (25 to 40μ) | 5 μg to 1 mg |
| Glucosamine sulfate | 100 to 300 mg |
| Magnesium ascorbic phosphate | 100 mg |
| Cellulose | 20 mg |
| Sucrose | 5 mg |

Formula 4

| Component | Amount |
| --- | --- |
| Insoluble Collagen Type II (25 to 40μ) | 5 μg to 1 mg |
| Glucosamine sulfate | 100 to 300 mg |
| Boron | 3 mg |
| Cellulose | 20 mg |
| Sucrose | 5 mg |

Formula 5

| Component | Amount |
| --- | --- |
| Insoluble Collagen Type II (25 to 40μ) | 20 μg |
| Glucosamine sulfate | 150 mg |
| Chondroitin sulfate | 200 mg |

EXAMPLES

Insoluble, unproteolyzed collagen Type II is prepared from the "keel" of the breast bone of healthy chickens using a process that leaves the collagen intact in its native form as described herein above.

To that end, one (1) kilogram (kg) of sternal chicken sternal cartilage was cleaned of all adhering soft tissue, including the perichondrium, and ground into small particles, 1–2 mm$^3$, using a Cuisinart food processor. To 980 grams of ground cartilage was added 1.8 liters of phosphate buffered saline and 1.9 grams of pepsin dissolved in 30 ml of distilled water. After stirring for 72 hours at 4° C. the residue was washed 3 times with 33 liters of 0.5 M acetic acid containing 1.0 M NaCl for 2 hours each time, and the residue was collected after each wash. The residue was then washed with 4.0 M NaCl in 0.05 M phosphate buffer, pH 7.4, and incubated at 4° C. for 16 hours in the same buffer. The residue was then washed with 20% aqueous ethyl alcohol until all the salt was removed to form about 63 grams of insoluble collagen residue. The insoluble collagen residue was then lyophilized and was shown to be pure type II collagen as evidenced by amino acid analysis. The insoluble collagen residue was then powdered under liquid nitrogen using a Spex mill to a size of about 25 to 40 micron diameter particles, used to prepare tablets according to Formula 5, and tested for effectiveness in alleviating rheumatoid arthritis.

The insoluble collagen Type II prepared according to the method described above has been tested for effectiveness in alleviating rheumatoid arthritis. Twenty micrograms of the collagen was administered as a tablet twice daily according to Formula 5, 30 minutes before breakfast and 30 minutes before dinner. Six patients with diagnosed rheumatoid arthritis lasting from 5 to 20 years, were treated. The results are shown in Table I.

TABLE I

| Patient | Time for pain to disappear (days) |
| --- | --- |
| Patient 1 | 5 |
| patient 2 | 7 |
| Patient 3 | 4 |
| Patient 4 | 10 |
| Patient 5 | 15 |
| Patient 6 | 7 |

This collagen has also been tested for effectiveness on dogs suffering from osteoarthritis, for effectiveness in relieving pain, as judged by the dog's range of motion. Of the 5 dogs treated, all improved as judged by their motion. In addition, in a dog that has been treated for 30 days, radiographic evidence shows that the cartilage has regenerated.

Although the foregoing has been described in some details by way of illustration and example, for the purposes of clarity and understanding, is obvious that certain changes and modifications may be practiced within the scope of the appended claims.

What is claimed is:

1. A method for treating rheumatoid arthritis or osteoarthritis in a patient comprising oral administration of an effective amount of a composition comprising collagen Type II and a compound selected from the group consisting of glucosamine or its salts and chondroitin sulfate and/or its salts.

2. The method of claim 1 wherein said collagen Type II is insoluble and in a particle size of 1 to 100 microns.

3. The method of claim 1 wherein said insoluble collagen Type II is prepared according to the method of claim 1.

4. The method of claim 1 wherein said effective amount comprises about 1 microgram to 5 milligrams of insoluble collagen Type II per 70 kilogram patient per day.

5. The method of claim 4 wherein said effective amount comprises about 40 micrograms of insoluble collagen Type II per 70 kilogram patient per day.

6. The method of claim 1 wherein the composition comprises collagen Type II and glucosamine salt.

7. The method of claim 6 wherein said effective amount comprises about 50 to 1000 milligrams of glucosamine per 70 kilogram patient per day.

8. The method of claim 6 wherein said glucosamine salt is glucosamine sulfate.

9. The method of claim 1 wherein the composition comprises collagen Type II and chondroitin salt.

10. The method of claim 9 wherein said effective amount comprises about 50 to 1000 milligrams of chondroitin per 70 kilogram patient per day.

11. The method of claim 9 wherein said chondroitin salt is chondroitin sulfate.

12. The method of claim 1 wherein said composition further comprises boron.

13. The method of claim 12 wherein said effective amount comprises about 0.5 to 20 milligrams of boron per kilogram patient per day.

14. The method of claim 1 wherein said composition further comprises ascorbic acid.

15. The method of claim 14 wherein said effective amount comprises about 1 to 500 milligrams of ascorbic acid per 70 kilogram patient per day.

16. The method of claim 1 wherein said composition further comprises a magnesium salt.

17. The method of claim 16 wherein said effective amount comprises about 0.1 to 10 milligrams of magnesium salt per 70 kilogram patient per day.

18. The method of claim 1 wherein the composition comprises collagen Type II, chondroitin sulfate, glucosamine sulfate and boron.

19. The method of claim 1 wherein the composition comprises collagen Type II, chondroitin sulfate, glucosamine sulfate and ascorbic acid.

20. The method of claim 1 wherein the composition comprises collagen Type II, chondroitin sulfate, glucosamine sulfate and magnesium salt.

21. The method of claim 1 wherein the patient suffers from osteoarthritis.

22. The method of claim 1 wherein the patient suffers from rheumatoid arthritis.

23. The method of claim 1 wherein said composition is formulated as a tablet.

24. The method of claim 1 wherein said composition is formulated as capsule.

25. The method of claim 1 wherein said composition is formulated as an aerosol spray.

26. The method of claim 1 wherein the dosages are administered from 1 to 6 times daily.

27. A therapeutic composition for treating arthritis comprising and effective amount of collagen Type II and a compound selected from the group consisting of glucosamine salt and chondroitin salt.

28. The composition of claim 27 wherein said collagen Type II is insoluble and in a particle size of 1.0 to 100 microns.

29. The composition of claim 27 wherein said insoluble collagen Type II is prepared according to the method of claim 1.

* * * * *